United States Patent [19]

Diana

[11] Patent Number: 4,945,164
[45] Date of Patent: Jul. 31, 1990

[54] 1,3,4-OXADIAZOLYL-PHENOXYALKYLISOXAZOLES AND THEIR USE AS ANTIVIRAL AGENTS AND INTERMEDIATES THEREOF

[75] Inventor: Guy D. Diana, Stephentown, N.Y.

[73] Assignee: Sterling Drug Inc., New York, N.Y.

[21] Appl. No.: 396,419

[22] Filed: Aug. 18, 1989

[51] Int. Cl.$^5$ ............................................. C07D 261/10
[52] U.S. Cl. .................................... 548/247; 548/143
[58] Field of Search ......................................... 548/247

[56] References Cited

U.S. PATENT DOCUMENTS 4,451,476  5/1984  Diana ................... 548/247
4,857,539  8/1989  Diana et al. ........... 514/378

FOREIGN PATENT DOCUMENTS 137242  4/1985  European Pat. Off. .
207453  1/1987  European Pat. Off. .

Primary Examiner—Anton M. Sutto
Assistant Examiner—E. Bernhardt

Attorney, Agent, or Firm—Thomas L. Johnson; Frederik W. Stonner; Paul E. Dupont

[57] ABSTRACT

Compounds of the formula

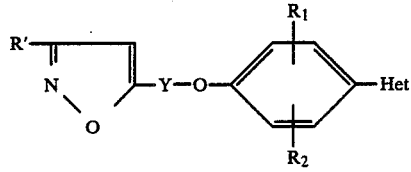

wherein:
Y is an alkylene bridge of 3–9 carbon atoms;
R' is lower-alkyl or hydroxy-lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
Het is selected from 1,3,4-oxadiazol-2-yl and 5-alkylated derivatives thereof, are useful as antiviral agents, particularly against picornaviruses, including numerous strains of rhinovirus.

3 Claims, No Drawings

1,3,4-OXADIAZOLYL-PHENOXYALKYLISOX-AZOLES AND THEIR USE AS ANTIVIRAL AGENTS AND INTERMEDIATES THEREOF

BACKGROUND OF THE INVENTION (a) Field of the Invention

This invention relates to novel heterocyclic substituted-phenoxyalkylisoxazoles and -furans, to methods for the preparation thereof, and compositions and methods for the use thereof as antiviral agents.

(b) Information Disclosure Statement

Diana U.S. Pat. No. 4,451,476, issued May 29, 1984, discloses antivirally active compounds having the formula wherein:

R is alkyl of 1 to 3 carbon atoms;

n is an integer from 4 to 8; and

Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

Sterling Drug Inc. European Patent Application Publ. No. 137,242, published Apr. 17, 1985, discloses antivirally active compounds having the formula wherein:

R, $R_1$, $R_2$, $R_3$ and $R_4$ are each hydrogen or alkyl of 1 to 3 carbon atoms optionally substituted by hydroxy, lower-alkanoyloxy, lower-alkoxy, chloro, or N=Z, wherein N=Z is amino, lower-alkanoylamino, lower-alkylamino, di-lower-alkylamino, 1-pyrrolidinyl, 1-piperidinyl or 4-morpholinyl; with the proviso that R is other than hydrogen;

$R_5$ is hydrogen, lower-alkyl, halogen, nitro, lower-alkoxy, lower-alkylthio or trifluoromethyl;

X is O or a single bond; and n is an integer from 3 to 9;

and to pharmaceutically acceptable acid-addition salts thereof.

Sterling Drug Inc. European Patent Application Publ. No. 207,453, published Jan. 7, 1987, discloses compounds of Formula I below where Het is 1,3,4-oxadiazol-5-yl.

SUMMARY OF THE INVENTION

The present invention relates to compounds of the formula wherein:

Y is an alkylene bridge of 3–9 carbon atoms;

Z is N or HC;

R is hydrogen or lower-alkyl of 1–5 carbon atoms, with the proviso that when Z is N, R is lower-alkyl;

$R_1$ and $R_2$ are hydrogen, halogen, lower-alkyl, lower-alkoxy, nitro, lower-alkoxycarbonyl or trifluoromethyl; and Het is selected from the group consisting of:

where n is 2 or 3; and $R_3$, $R_4$ and $R_5$ are hydrogen or lower-alkyl of 1-5 carbon atoms;

$R_6$ is hydrogen, lower-alkyl of 1-5 carbon atoms or chloro;

$R_7$ is hydrogen, or alkyl or hydroxyalkyl of 1-5 carbon atoms;

or pharmaceutically acceptable acid-addition salts of basic members thereof.

A preferred class of compounds within the scope of Formula I are those of the formula

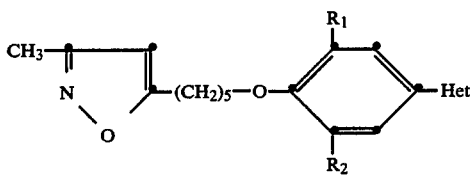    II

The invention also relates to compositions for combating viruses comprising an antivirally effective amount of a compound of Formulas I or II in admixture with a suitable carrier or diluent, and to methods of combating viruses therewith, including the systemic treatment of viral infections in a mammalian host.

DETAILED DESCRIPTION INCLUSIVE OF PREFERRED EMBODIMENTS

The compounds of Formula I where Het is a nitrogen-containing heterocyclic group are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

When the term halogen is used to define the substituents $R_1$ and $R_2$, any of the four common halogens, fluorine, chlorine, bromine or iodine are contemplated; and the term lower-alkoxycarbonyl refers to such groups having from two to four carbon atoms.

The compounds of Formula I can be prepared by a process which comprises reacting a compound of the formula

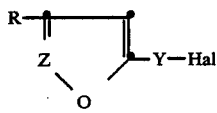    III wherein Hal is chlorine, bromine or iodine, with an alkali metal salt of a compound of the formula

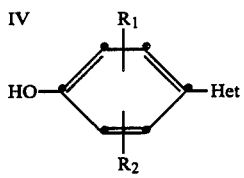    IV

The compounds of Formula I can also be prepared by an alternative process which comprises reacting a compound of the formula

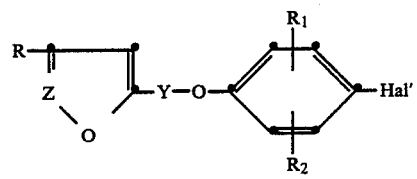    V where Hal' is bromine or iodine, with a compound of the formula

    VI (R')$_3$Sn-Het' where R' is lower-alkyl of 1-6 carbon atoms, and Het' is any of the aromatic type heterocyclic groups included in the definition of Het in Formula I; in the presence of a palladium complex catalyst.

The process for the preparation of compounds of Formula I by reacting intermediates of Formulas III and IV takes place by heating the reactants in an inert solvent in the presence of an alkali metal base, e.g. potassium carbonate or potassium hydroxide at a temperature between about 50° C. and 150° C.

The intermediates of Formula III where Z is N are prepared by reacting an alkali metal derivative of an isoxazole of the formula

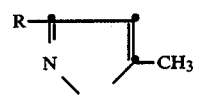    VII with a dihalide, Hal-Y'-Hal, where Y' is an alkylene bridge of 2 to 8 carbon atoms. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula III where Z is HC are prepared from the appropriate omega-(2-furan)alkanoic acid by reduction to the corresponding alcohol and replacement of the hydroxy group by halogen; or by direct alkylation of furan with a dihalide, Hal-Y-Hal, in the presence of a strong base such as butyllithium.

The intermediates of Formula IV are a generically known class of heterocyclic substituted phenols, prepared as described hereinafter in the general description and specific examples.

In the alternative process comprising reacting compounds of Formulas V and VI, the process is carried out using approximately equimolar amounts of the reactants in an inert solvent at a temperature between about 50° C. and 100° C., conveniently at the reflux temperature of the solvent. The reaction is complete in a period ranging from 5-24 hours. The palladium complex catalyst, present to the extent of about 5 mole percent, can be any such catalyst known to effect cross-coupling of organotin compounds with organic halides [cf. Kosugi et al., Bull. Chem. Soc. Japan 59, 677-679 (1986)], for example PdCl$_2$-(PPh$_3$)$_2$, Pd(PPh$_3$)$_4$, PdCl$_2$[P(o-tolyl)$_3$]$_2$, PdCl$_2$+2P(OEt)$_3$ and PdCl$_2$(PhCN)$_2$. A preferred catalyst is dichlorobis(triphenylphosphine)palladium [PdCl$_2$(PPh$_3$)$_2$].

The intermediates of Formula V are prepared by reacting an alkali metal salt of a phenol of the formula

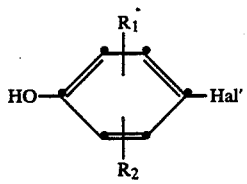

with a compound of Formula III in a procedure analogous to that of the reaction of III with IV.

The organotin reagent of Formula VI is prepared by known procedures comprising reacting a tri-lower-alkyltin halide with an unsubstituted aromatic heterocycle in the presence of a strong base such as butyllithium under anhydrous conditions. The trialkyltin moiety enters the most reactive position on the heterocyclic ring; however, the trialkyltin moiety can be directed to other positions on the heterocyclic ring by using the appropriate halo-substituted heterocycle.

Certain compounds of the invention can be prepared by construction of the Het ring from intermediates having a cyano or formyl group on the phenyl ring, as follows.

The compounds of Formula I where Het is a 4,5-dihydro-1H-imidazolyl group:

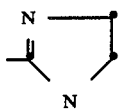

are prepared from the corresponding cyanophenyl compounds of the formula

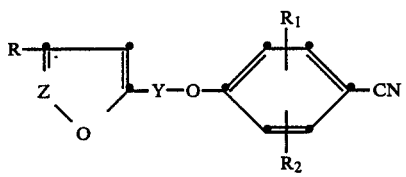

by heating the latter with ethylenediamine in acid medium. The compounds of Formula IX are in turn prepared from the appropriate cyanophenol and a compound of Formula III.

The compounds of Formula I where Het is a 2-thiazolyl group:

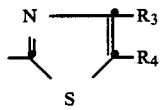

are prepared from the corresponding cyanophenyl compounds of Formula IX by conversion of the latter to the corresponding thioamide with hydrogen sulfide in pyridine, and then reacting the thioamide with a haloalkanone, $R_3CH(Hal)$—CO—$R_4$.

The compounds of Formula I where Het is a tetrazole group:

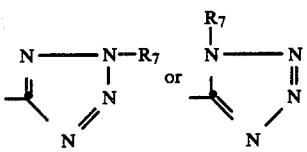

are prepared from the corresponding cyanophenyl compounds of Formula IX by reaction of the latter with sodium azide to give a tetrazole when $R_7$ is hydrogen. Treatment of the latter with a lower-alkyl halide or hydroxy-lower-alkyl halide in the presence of a base gives both isomeric tetrazoles where $R_7$ is lower-alkyl or hydroxy-lower-alkyl.

The compounds of Formula I where Het is a group of the formula

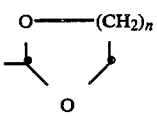

are prepared by conventional cyclic acetal formation by reacting a benzaldehyde derivative of the formula

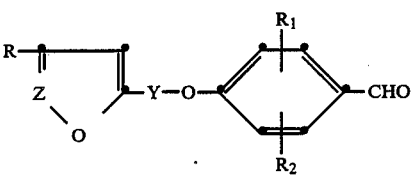

with ethylene glycol or propylene glycol. The compounds of Formula X are in turn prepared by reacting the appropriate 4-hydroxybenzaldehyde with a compound of Formula III.

The compounds of Formula I where Het is a 2-thiazolidinyl group:

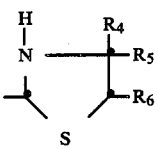

are prepared by reacting a benzaldehyde derivative of Formula X with an amino alkanethiol, $H_2N$—$C(R_4R_5)CH(R_6)$—SH, heated in a non-polar organic solvent with an acid catalyst.

The compounds of Formula I where Het is a 4-triazolyl group:

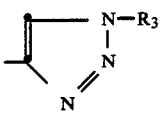

are prepared by reacting a cyanophenyl compound of the Formula IX with the lithium derivative of a N-nitrosoamine, $R_3(CH_3)N$—N=O according to the procedure of Seebach et al., Angew. Chem., International Ed. 11, 1102 (1972).

The compounds of Formula I where Het is a 4,5-dihydro-3H-pyrrol-2-yl group:

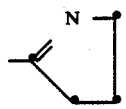

can be prepared by reacting a compound of Formula V with 1-trimethylsilylpyrrolidin-2-one according to the procedure described by Feringa and Jansen, Tetrahedron Letters 507 (1986).

The invention also contemplates compounds of the formula:

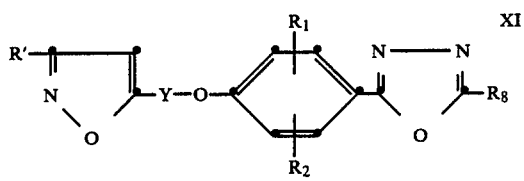

where R' is lower-alkyl or hydroxy-lower-alkyl of 1–5 carbon atoms, $R_8$ is hydrogen or lower-alkyl of 1–5 carbon atoms, and Y, $R_1$ and $R_2$ have the meanings given hereinabove. The compounds of Formula XI are prepared by reacting a compound of Formula III (Z is N, and R is R') with a compound of Formula IV where Het is 1,3,4-oxadiazol-2-yl or 5-lower-alkyl-1,3,4-oxadiazol-2-yl. The latter phenolic compounds of Formula IV are prepared as described in U.S. Pat. No. 4,218,458, issued Aug. 19, 1980.

Alternatively, the compounds of Formula XI can be prepared by cyclization of compounds of the formula

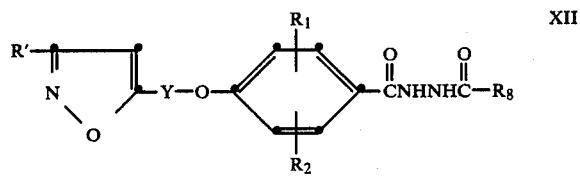

by reaction with hexamethyldisilazane in the presence of tetrabutylammonium trifluoride according to the method of Rigo et al., Synthetic Communications 16, 1665–9 (1986). The intermediate acylhydrazines of Formula XII are also part of the invention and are prepared from the corresponding carboxylic acids:

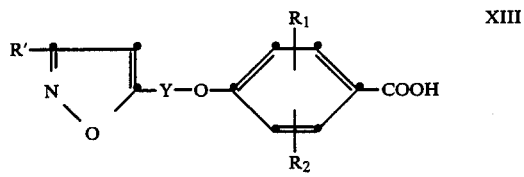

by conventional amide formation. The acid XIII is conveniently prepared by hydrolysis of the nitrile of Formula IX (Z is H, R is R').

The structures of the compounds of the invention were established by the modes of synthesis, by elementary analysis, and by infrared and nuclear magnetic resonance spectra.

The following examples will further illustrate the invention.

EXAMPLE 1

3-Methyl-5-{5-[4-(1,3,4-oxadiazol-2-yl)phenoxy]pentyl}-isoxazole [II; $R_1$ and $R_2$=H, Het=2-(1,3,4-oxadiazolyl)].

A mixture of 23.6 g 4-(1,3,4-oxadiazolyl)phenol (U.S. Pat. No. 4,218,458, Example XIX), 35 g 5-(5-bromopentyl)-3-methylisoxazole and 40 g milled potassium carbonate in 1.5 liters acetonitrile under nitrogen was heated to reflux. A catalytic amount of sodium iodide was added and refluxing continued for 4 hrs. The reaction mixture was filtered and concentrated to a solid residue. The latter was dissolved in ethyl acetate and the solution washed with water and saturated sodium chloride solution, dried over magnesium sulfate and concentrated in vacuo. The residue was recrystallized from triethylamine to give 18.5 g 3-methyl-5-{5-[4-(1,3,4-oxadiazol-2-yl)phenoxy]pentyl}isoxazole, white needles, m.p. 84°–86° C.

EXAMPLE 2

(a) 3,5-Dichloro-4-hydroxybenzoic acid hydrazide.

A mixture of 10.0 g methyl 3,5-dichloro-4-hydroxybenzoate and 15 ml hydrazine hydrate was warmed on a steam bath for 3 hrs. Excess hydrazine was removed in vacuo and the residue recrystallized from 2-propanol-water (80:20) to give 9 g of the hydrazide, used directly in the next reaction.

(b) 2,6-Dichloro-4-(1,3,4-oxadiazol-2-yl)phenol [IV; $R_1$=2-Cl, $R_2$=6-Cl, Het=1,3,4-oxadiazol-2-yl].

A mixture of 8.9 g 3,5-dichloro-4-hydroxybenzoic acid hydrazide and 500 ml triethyl orthoformate was stirred and heated at reflux for 4 hrs. The solvent was removed in vacuo to afford the product (9.9 g) as a yellow solid, used directly in the next reaction.

(c)

5-{5-[3,5-Dichloro-4-(1,3,4-oxadiazol-2-yl)phenoxy]-pentyl}-3-methylisoxazole [II; $R_1$ and $R_2$=Cl, Het=1,3,4-oxadiazol-2-yl] was prepared from 8.5 g 2,6-dichloro-4-(1,3,4-oxadiazol-2-yl)phenol and 20 g 5-(5-bromopentyl)-3-methylisoxazole according to the procedure of Example 1, and was obtained in 34% yield (4.8 g), m.p. 73°–74° C. when recrystallized from triethylamine.

It is further contemplated that by substituting for the 5-(5-bromopentyl)-3-methylisoxazole in the foregoing procedure a molar equivalent amount of 5-(5-chloropentyl)-3-hydroxymethylisoxazole there can be prepared 5-{5-[3,5-dichloro-4-(1,3,4-oxadiazol-2-yl)phenoxy]pentyl}-3-hydroxymethylisoxazole [XI; R'=HOCH$_2$, $R_1$ and $R_2$=Cl, Y=(CH$_2$)$_5$]. The intermediate 5-(5-chloropentyl)-3-hydroxymethylisoxazole was prepared by reacting 1-bromo-4-chlorobutane with 3-hydroxymethyl-5-methylisoxazole in the presence of n-butyllithium. The 3-hydroxymethyl-5-methylisoxazole (b.p. 77°–80° C., 0.5 mm) was in turn prepared by reduction of methyl 5-methylisoxazole-3-carboxylate with lithium aluminum hydride.

EXAMPLE 3

(a)

3,5-Dichloro-4-[5-(3-methylisoxazol-5-yl)pentyloxy]-benzoic acid [XIII; R'=CH$_3$, Y=(CH$_2$)$_5$, R$_1$ and R$_2$=3,5-Cl$_2$].

A mixture of 6.11 g 5-[5-(2,6-dichloro-4-cyanophenoxy)pentyl]-3-methylisoxazole (m.p. 59°–60° C.), 75 ml 35% sodium hydroxide and 75 ml ethanol was stirred on a steam bath for several hours. The reaction mixture upon standing separated into a clear lower layer and a yellow upper layer. The latter was separated, diluted with cold water and acidified with hydrochloric acid. The resulting solid was collected and recrystallized from acetonitrile to give 5.24 g 3,5-dichloro-4-[5-(3-methylisoxazol-5-yl)pentyloxy]benzoic acid, m.p. 67°–69° C.

(b)

N-Acetyl-N'-{3,5-dichloro-4-[5-(3-methylisoxazol-5-yl)pentyloxy]benzoyl}hydrazine [XII; R'=CH$_3$, Y=(CH$_2$)$_5$, R$_1$ and R$_2$=3,5-Cl$_2$, R$_8$=CH$_3$].

A solution of 5.19 g of the product of part (a) and 2.59 g carbonyldiimidazole in 50 ml tetrahydrofuran (THF) in a nitrogen atmosphere was heated at reflux until gas evolution ceased. The mixture was cooled and 1.18 g acetylhydrazine added. The resulting mixture was heated at reflux for 5–6 hours and then concentrated in vacuo. The residue was dissolved in ethyl acetate and filtered through a plug of silica gel. There was isolated a colorless solid (1.49 g), N-acetyl-N'-{3,5-dichloro-4-[5-(3-methylisoxazol-5-yl)pentyloxy]benzoyl}hydrazine, m.p. (polymorphic) 118° and 134° C. when recrystallized from isopropyl acetate.

(c)

5-{5-[3,5-Dichloro-4-(5-methyl-1,3,4-oxadiazol-2-yl)phenoxy]pentyl}-3-methylisoxazole [XI; R'=CH$_3$, Y=(CH$_2$)$_5$, R$_1$ and R$_2$=3,5-Cl$_2$, R$_8$=CH$_3$].

A mixture of 0.94 g of the product of part (b), 1 ml hexamethyldisilazane, 0.5 ml tetrabutylammonium fluoride and 10 ml chlorobenzene was heated to 125° C. under nitrogen with stirring. A catalytic amount of imidazole as a silylating catalyst was then added. After one-half hour an additional 0.5 ml hexamethyldisilazane and a catalytic amount of tetrabutylammonium fluoride were added and the reaction mixture heated at 125° C. for three days. The mixture was then cooled and filtered through a plug of silica gel and eluted with ethyl acetate. The product isolated from the filtrate was recrystallized from isopropyl acetate-hexane to give 0.53 g 5-{5-[3,5-dichloro-4-(5-methyl-1,3,4-oxadiazol-2-yl)phenoxy]pentyl}-3-methylisoxazole, light tan solid, m.p. 71°–72° C.

It is further contemplated that by replacing the 5-[5-(2,6-dichloro-4-cyanophenoxy)pentyl]-3-methylisoxazole in part (a) of the foregoing example by a molar equivalent amount of 5-[5-(2,6-dimethyl-4-cyanophenoxy)pentyl]-3-hydroxymethylisoxazole there can be prepared N-acetyl-N'-{3,5-dimethyl-4-[5-(3-hydroxymethylisoxazol-5-yl)pentyloxy]benzoyl}hydrazine [XII; R'=HOCH$_2$, Y=(CH$_2$)$_5$, R$_1$ and R$_2$=3,5-(CH$_3$)$_2$, R$_8$=CH$_3$] and 5-{5-[3,5-dimethyl-4-(5-methyl-1,3,4-oxadiazol-2-yl)phenoxy]pentyl}-3-hydroxymethylisoxazole [XI; R'=HOCH$_2$, Y=(CH$_2$)$_5$, R$_1$ and R$_2$=3,5-(CH$_3$)$_2$, R$_8$=CH$_3$]. The intermediate 5-[5-(2,6-dimethyl-4-cyanophenoxy)pentyl]-3-hydroxymethylisoxazole (yellowish-tan solid, m.p. 63°–64° C. from diethyl ether) was prepared from 2,6-dimethyl-4-cyanophenol and 5-(5-chloropentyl)-5-hydroxymethylisoxazole.

EXAMPLE 4

(a) Ethyl 3,5-dichloro-4-[3-(3-methylisoxazol-5-yl)propyloxy]-benzoate.

To a mixture of 10.05 g ethyl 3,5-dichloro-4-hydroxybenzoate and 8.0 g 5-(3-chloropropyl)-3-methylisoxazole in 550 ml dry acetonitrile was added 4.87 g potassium hydroxide and 12.9 g potassium iodide. The reaction mixture was stirred at reflux overnight and then filtered and concentrated in vacuo. The residue was partitioned between ethyl acetate and water and the organic layer concentrated to a yellow oil. The latter was crystallized from ethyl acetate-hexane (1:4) at −50° C. to give 14 g of product, 12 g of which was used directly in the following hydrolysis reaction. A sample of the ester was purified by chromatography on silica to give pure compound, m.p. 49°–50° C.

(b)

3,5-Dichloro-4-[3-(3-methylisoxazol-5-yl)propyloxy]-benzoic acid [XIII; R'=CH$_3$, Y=(CH$_2$)$_3$, R$_1$ and R$_2$=3,5-Cl$_2$] was prepared by hydrolysis of 12 g of the crude product from part (a) with 120 ml 10% sodium hydroxide in 120 ml ethanol, stirred at reflux for two hours. The reaction mixture was acidified and the product isolated to give 9 g 3,5-dichloro-4-[3-(3-methylisoxazol-5-yl)propyloxy]benzoic acid, m.p. 156°–157° C. when recrystallized from isopropyl acetate-hexane (1:1).

(c)

N-Acetyl-N'-{3,5-dichloro-4-[3-(3-methylisoxazol-5-yl)propyloxy]benzoyl}hydrazine [XII; R'=CH$_3$, Y=(CH$_2$)$_3$, R$_1$ and R$_2$=3,5-Cl$_2$, R$_8$=CH$_3$] was prepared from 8.3 g of the product of part (b) according to the procedure of Example 3, part (b), and was obtained (10.2 g) in the form of a colorless solid, m.p. 141°–142° C. when recrystallized from ethyl acetate-hexane (1:1).

(d)

5-{3-[3,5-Dichloro-4-(5-methyl-1,3,4-oxadiazol-2-yl)phenoxy]propyl}-3-methylisoxazole [XI; R'=CH$_3$, Y=(CH$_2$)$_3$, R$_1$ and R$_2$=3,5-Cl$_2$, R$_8$=CH$_3$] was prepared from 10 g of the product of part (c) according to the procedure of Example 3, part (c), and was obtained (0.6 g after chromatography on silica) in the form of a colorless solid, m.p. 99°–100° C. when recrystallized from isopropyl acetate.

Biological evaluation of compounds of Formulas I and II has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Wisconsin) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A, -1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention. For some of the compounds, the $MIC_{50}$ and $MIC_{80}$ values are based on the testing of fewer than 15 rhinovirus serotypes. In these cases the number of serotypes (N) is indicated in parentheses after the $MIC_{80}$ figure.

| Example No. | MIC (Polio 2) | $MIC_{50}$ (Rhinovirus) | $MIC_{80}$ (N) (Rhinovirus) |
| --- | --- | --- | --- |
| 1 | 0.05 | | 2.56 (1) |
| 2(c) | 2.24 | 0.25 | 0.91 |
| 3(c) | | 0.14 | 0.46 (15) |
| 4(d) | | 0.054 | 0.35 (6) |

The following Table compares the MIC values for the compound of Example 2(c) and the methylated derivative of Example 3(c) against 15 rhinovirus serotypes:

| Serotype | Example 2(c) | Example 3(c) |
| --- | --- | --- |
| 1A | 1.45 | 0.44 |
| 1B | 0.53 | 0.14 |
| 2 | 0.41 | 0.016 |
| 6 | 7.06 | 0.46 |
| 14 | 2.02 | 0.19 |
| 15 | 1.92 | 0.42 |
| 21 | 0.24 | 0.0092 |
| 22 | 0.45 | 0.018 |
| 25 | 2.42 | 0.7 |
| 30 | 0.10 | 0.031 |
| 41 | 2.76 | 99* |
| 50 | 0.091 | 0.041 |
| 67 | 0.64 | 0.1 |
| 86 | 1.28 | 0.57 |
| 89 | 0.28 | 0.01 |

*Inactive at dose levels tested

The foregoing data show that, except in the case of serotype 41, the compound of Example 3(c) is substantially more active than the compound of Example 2(c).

The antiviral compositions are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration.

I claim:

1. A compound of the formula

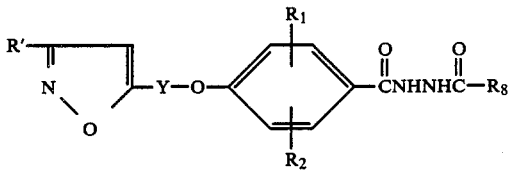

wherein:

Y is an alkylene bridge of 3–9 carbon atoms;

R' is lower-alkyl or hydroxy-lower-alkyl of 1–5 carbon atoms;

$R_1$ and $R_2$ are hydrogen, halogen, lower-alkyl, lower-alkoxy, nitro, lower-alkylcarbonyl or trifluoromethyl; and $R_8$ is hydrogen or lower-alkyl of 1–5 carbon atoms.

2. N-Acetyl-N'-{3,5-dichloro-4-[5-(3-methylisoxazol-5-yl)pentyloxy]benzoyl}hydrazine, according to claim 1.

3. N-Acetyl-N'-{3,5-dichloro-4-[3-(3-methylisoxazol-5-yl)propyloxy]benzoyl}hydrazine, according to claim 1.

* * * * *